(12) United States Patent
Gilbeau

(10) Patent No.: US 8,389,777 B2
(45) Date of Patent: Mar. 5, 2013

(54) CONTINUOUS METHOD FOR MAKING CHLORHYDRINES

(75) Inventor: Patrick Gilbeau, Braine-le-Comte (BE)

(73) Assignee: Solvay (Société Anonyme), Brussels (BE)

( * ) Notice: Subject to any disclaimer, the term of this patent is extended or adjusted under 35 U.S.C. 154(b) by 848 days.

(21) Appl. No.: 11/915,053

(22) PCT Filed: May 19, 2006

(86) PCT No.: PCT/EP2006/062463
§ 371 (c)(1), (2), (4) Date: Nov. 20, 2007

(87) PCT Pub. No.: WO2006/106154
PCT Pub. Date: Oct. 12, 2006

(65) Prior Publication Data
US 2008/0194851 A1 Aug. 14, 2008

Related U.S. Application Data

(60) Provisional application No. 60/734,635, filed on Nov. 8, 2005, provisional application No. 60/734,657, filed on Nov. 8, 2005, provisional application No. 60/734,636, filed on Nov. 8, 2005, provisional application No. 60/734,627, filed on (Continued)

(30) Foreign Application Priority Data

May 20, 2005 (EP) .................................. 05104321
May 20, 2005 (FR) .................................. 05 05120

(51) Int. Cl.
*C07C 31/34* (2006.01)
*C07D 301/24* (2006.01)

(52) U.S. Cl. .................... 568/844; 568/841; 549/521
(58) Field of Classification Search .................. 568/841, 568/844; 549/521
See application file for complete search history.

(56) References Cited

U.S. PATENT DOCUMENTS

| | | | |
|---|---|---|---|
| 280,893 | A | 7/1883 | Baujard |
| 865,727 | A | 9/1907 | Queneau |
| 2,060,715 | A | 11/1936 | Arvin |
| 2,063,891 | A | 12/1936 | Dreyfus |
| 2,144,612 | A | 1/1939 | Britton et al. |

(Continued)

FOREIGN PATENT DOCUMENTS

| | | |
|---|---|---|
| BE | 422877 | 8/1937 |
| CA | 1119320 | 8/2003 |

(Continued)

OTHER PUBLICATIONS

U.S. Appl. No. 11/914,879, filed Nov. 19, 2007, Gilbeau.

(Continued)

*Primary Examiner* — Taylor Victor Oh
(74) *Attorney, Agent, or Firm* — Oblon, Spivak, McClelland, Maier & Neustadt, L.L.P.

(57) ABSTRACT

Continuous process for producing a chlorohydrin, wherein a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition comprises the polyhydroxylated aliphatic hydrocarbon and esters of the polyhydroxylated aliphatic hydrocarbon whose sum content, expressed as moles of polyhydroxylated aliphatic hydrocarbon, is greater than 1.1 mol % and less than or equal to 30 mol %, the percentage being based on the organic part of the liquid reaction medium.

18 Claims, 1 Drawing Sheet

Related U.S. Application Data

Nov. 8, 2005, provisional application No. 60/734,634, filed on Nov. 8, 2005, provisional application No. 60/734,658, filed on Nov. 8, 2005, provisional application No. 60/734,637, filed on Nov. 8, 2005, provisional application No. 60/734,659, filed on Nov. 8, 2005.

(56) References Cited

U.S. PATENT DOCUMENTS

| | | | |
|---|---|---|---|
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,505,735 | A | 4/1950 | Halbedel |
| 2,726,072 | A | 12/1955 | Hermann |
| 2,811,227 | A | 10/1957 | O'Connor |
| 2,829,124 | A | 4/1958 | Napravnik et al. |
| 2,860,146 | A | 11/1958 | Furman et al. |
| 2,875,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,052,612 | A | 9/1962 | Henegar et al. |
| 3,061,615 | A | 10/1962 | Viriot et al. |
| 3,121,727 | A | 2/1964 | Baliker et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,260,059 | A | 7/1966 | Rosenberg et al. |
| 3,341,491 | A | 9/1967 | Robinson et al. |
| 3,355,511 | A | 11/1967 | Schwarzer |
| 3,385,908 | A | 5/1968 | Schwarzer |
| 3,445,197 | A | 5/1969 | Resh et al. |
| 3,457,282 | A | 7/1969 | Polak et al. |
| 3,618,295 | A | 11/1971 | Geiger et al. |
| 3,711,388 | A | 1/1973 | Gritzner |
| 3,766,221 | A | 10/1973 | Becker |
| 3,823,193 | A * | 7/1974 | Fernholz et al. .............. 568/848 |
| 3,839,169 | A | 10/1974 | Moyer |
| 3,865,886 | A | 2/1975 | Schindler et al. |
| 3,867,166 | A | 2/1975 | Sullivan |
| 3,879,180 | A | 4/1975 | Hutgens et al. |
| 3,954,581 | A | 5/1976 | Carlin |
| 3,968,178 | A | 7/1976 | Obrecht et al. |
| 4,003,723 | A | 1/1977 | Schafer et al. |
| 4,011,251 | A | 3/1977 | Tjurin et al. |
| 4,024,301 | A | 5/1977 | Witenhafer et al. |
| 4,127,594 | A | 11/1978 | Anderson et al. |
| 4,173,710 | A | 11/1979 | Boulet et al. |
| 4,197,399 | A | 4/1980 | Noel et al. |
| 4,220,529 | A | 9/1980 | Daude-Lagrave |
| 4,240,885 | A | 12/1980 | Suciu et al. |
| 4,255,470 | A | 3/1981 | Cohen et al. |
| 4,309,394 | A | 1/1982 | Hudson |
| 4,390,680 | A | 6/1983 | Nelson |
| 4,405,465 | A | 9/1983 | Moore et al. |
| 4,415,460 | A | 11/1983 | Suciu et al. |
| 4,464,517 | A | 8/1984 | Makino et al. |
| 4,499,255 | A | 2/1985 | Wang et al. |
| 4,560,812 | A | 12/1985 | Blytas |
| 4,595,469 | A | 6/1986 | Foller |
| 4,599,178 | A | 7/1986 | Blytas |
| 4,609,751 | A | 9/1986 | Hajjar |
| 4,634,784 | A | 1/1987 | Nagato et al. |
| 4,655,879 | A | 4/1987 | Brockmann et al. |
| 4,935,220 | A | 6/1990 | Schneider et al. |
| 4,960,953 | A | 10/1990 | Jakobson et al. |
| 4,973,763 | A | 11/1990 | Jakobson et al. |
| 4,990,695 | A | 2/1991 | Buenemann et al. |
| 5,041,688 | A | 8/1991 | Jakobson et al. |
| 5,200,163 | A | 4/1993 | Henkelmann et al. |
| 5,278,260 | A | 1/1994 | Schaffner et al. |
| 5,286,354 | A | 2/1994 | Bard et al. |
| 5,344,945 | A | 9/1994 | Grunchard |
| 5,359,094 | A | 10/1994 | Teles et al. |
| 5,393,428 | A | 2/1995 | Dilla et al. |
| 5,445,741 | A | 8/1995 | Dilla et al. |
| 5,478,472 | A | 12/1995 | Dilla et al. |
| 5,486,627 | A | 1/1996 | Quarderer, Jr. et al. |
| 5,567,359 | A | 10/1996 | Cassidy et al. |
| 5,578,740 | A | 11/1996 | Au et al. |
| 5,710,350 | A | 1/1998 | Jeromin et al. |
| 5,731,476 | A | 3/1998 | Shawl et al. |
| 5,744,655 | A | 4/1998 | Thomas et al. |
| 5,779,915 | A | 7/1998 | Becker et al. |
| 5,908,946 | A | 6/1999 | Stern et al. |
| 5,993,974 | A | 11/1999 | Fukushima et al. |
| 6,103,092 | A | 8/2000 | Silva |
| 6,111,153 | A | 8/2000 | Crow et al. |
| 6,142,458 | A | 11/2000 | Howk |
| 6,177,599 | B1 | 1/2001 | Cowfer et al. |
| 6,270,682 | B1 | 8/2001 | Santen et al. |
| 6,288,248 | B1 | 9/2001 | Strebelle et al. |
| 6,288,287 | B2 | 9/2001 | Ueoka et al. |
| 6,333,420 | B1 * | 12/2001 | Aoki et al. .............. 549/514 |
| 6,350,888 | B1 | 2/2002 | Strebelle et al. |
| 6,350,922 | B1 | 2/2002 | Vosejpka et al. |
| 6,719,957 | B2 | 4/2004 | Brady, Jr. et al. |
| 6,740,633 | B2 | 5/2004 | Norenberg et al. |
| 6,806,396 | B2 | 10/2004 | Gelblum et al. |
| 7,126,032 | B1 | 10/2006 | Aiken |
| 7,128,890 | B2 | 10/2006 | Ollivier |
| 7,473,809 | B2 * | 1/2009 | Kubicek et al. .............. 568/841 |
| 7,584,629 | B2 | 9/2009 | Sohn et al. |
| 2001/0014763 | A1 | 8/2001 | Ueoka et al. |
| 2003/0209490 | A1 | 11/2003 | Camp et al. |
| 2004/0016411 | A1 | 1/2004 | Joyce et al. |
| 2004/0024244 | A1 | 2/2004 | Walsdorff et al. |
| 2004/0047781 | A1 | 3/2004 | Becenel, Jr. |
| 2004/0150123 | A1 | 8/2004 | Strofer et al. |
| 2004/0179987 | A1 | 9/2004 | Oku et al. |
| 2004/0232007 | A1 | 11/2004 | Carson et al. |
| 2005/0115901 | A1 | 6/2005 | Heuser et al. |
| 2005/0261509 | A1 | 11/2005 | Delfort et al. |
| 2006/0052272 | A1 | 3/2006 | Meli et al. |
| 2006/0079433 | A1 | 4/2006 | Hecht et al. |
| 2006/0123842 | A1 | 6/2006 | Sohn et al. |
| 2007/0112224 | A1 | 5/2007 | Krafft et al. |
| 2007/0293707 | A1 | 12/2007 | Wolfert et al. |
| 2008/0053836 | A1 | 3/2008 | Bulan et al. |
| 2008/0146753 | A1 | 6/2008 | Woike et al. |
| 2008/0154050 | A1 | 6/2008 | Gilbeau |
| 2008/0281132 | A1 | 11/2008 | Krafft et al. |
| 2009/0022653 | A1 | 1/2009 | Strebelle et al. |
| 2009/0173636 | A1 | 7/2009 | Ooms et al. |
| 2009/0198041 | A1 | 8/2009 | Krafft et al. |
| 2010/0029959 | A1 | 2/2010 | Fan et al. |

FOREIGN PATENT DOCUMENTS

| | | |
|---|---|---|
| CN | 1296003 A | 5/2001 |
| CN | 101041421 | 9/2007 |
| DE | 58396 | 8/1891 |
| DE | 180 668 | 1/1906 |
| DE | 197 308 | 11/1906 |
| DE | 238 341 | 3/1908 |
| DE | 869 193 | 3/1953 |
| DE | 1 041 488 | 10/1958 |
| DE | 1 075 103 | 2/1960 |
| DE | 1 226 554 | 10/1966 |
| DE | 2 241 393 | 2/1974 |
| DE | 25 21 813 | 12/1975 |
| DE | 30 03 819 | 8/1981 |
| DE | 216 471 | 6/1983 |
| DE | 32 43 617 | 5/1984 |
| DE | 37 21 003 | 6/1987 |
| DE | 43 02 306 | 8/1994 |
| DE | 43 35 311 | 4/1995 |
| DE | 102 03 914 | 1/2002 |
| DE | 102 54 709 | 6/2004 |
| DE | 2384341 | 3/2008 |
| DE | 197 309 | 4/2008 |
| EP | 0 296 341 | 12/1988 |

| | | | | | | |
|---|---|---|---|---|---|---|
| EP | 0 347 618 | 12/1989 | | JP | 61-044833 | 3/1986 |
| EP | 0 421 379 | 4/1991 | | JP | 61-112066 | 5/1986 |
| EP | 0 452 265 | 10/1991 | | JP | 61-140532 | 6/1986 |
| EP | 0 518 765 | 12/1992 | | JP | 61-236749 | 10/1986 |
| EP | 0 522 382 | 1/1993 | | JP | 62-242638 | 10/1987 |
| EP | 0 535 949 | 4/1993 | | JP | 63-195288 | 8/1988 |
| EP | 0 563 720 | 10/1993 | | JP | 2-137704 | 5/1990 |
| EP | 0 568 389 | 11/1993 | | JP | 03-014527 | 1/1991 |
| EP | 0 582 201 | 2/1994 | | JP | 3-223267 | 10/1991 |
| EP | 0 618 170 | 10/1994 | | JP | 03-223267 | 10/1991 |
| EP | 0 916 624 | 5/1999 | | JP | 04-089440 | 3/1992 |
| EP | 0 919 551 | 6/1999 | | JP | 04-217637 | 8/1992 |
| EP | 0 774 450 | 2/2000 | | JP | 60-009589 | 1/1994 |
| EP | 1 059 278 | 12/2000 | | JP | 6-25196 | 4/1994 |
| EP | 1 106 237 | 6/2001 | | JP | 6-184024 | 7/1994 |
| EP | 1 153 887 | 11/2001 | | JP | 06-321852 | 11/1994 |
| EP | 1 163 946 | 12/2001 | | JP | 08-003087 | 1/1996 |
| EP | 1 231 189 | 8/2002 | | JP | 8-59593 | 3/1996 |
| EP | 1 298 154 | 4/2003 | | JP | 09-299953 | 11/1997 |
| EP | 0 561 441 | 9/2003 | | JP | 10-139700 | 5/1998 |
| EP | 1 411 027 | 4/2004 | | JP | 10-218810 | 8/1998 |
| EP | 1 752 435 | 2/2007 | | JP | 2000-344692 | 12/2000 |
| EP | 1 752 436 | 2/2007 | | JP | 2001-037469 | 2/2001 |
| EP | 1 760 060 | 3/2007 | | JP | 2001-213827 | 8/2001 |
| EP | 1 762 556 | 3/2007 | | JP | 2001-261308 | 9/2001 |
| EP | 1 770 081 | 4/2007 | | JP | 2001-1261581 | 9/2001 |
| EP | 1 772 446 | 4/2007 | | JP | 2001-276572 | 10/2001 |
| EP | 1 775 278 | 4/2007 | | JP | 2002-02033 | 1/2002 |
| EP | 2 085 364 | 8/2009 | | JP | 2002-038195 | 2/2002 |
| FR | 1 306 231 | 10/1961 | | JP | 2002-265986 | 9/2002 |
| FR | 1 417 386 | 10/1964 | | JP | 2002-363153 | 12/2002 |
| FR | 1 476 073 | 4/1966 | | JP | 2003-81891 | 3/2003 |
| FR | 1 577 792 | 8/1968 | | JP | 2003-89680 | 3/2003 |
| FR | 2 180 138 | 5/1973 | | JP | 2003-183191 | 7/2003 |
| FR | 2 217 372 | 1/1974 | | JP | 2003-206473 | 7/2003 |
| FR | 2 565 229 | 12/1985 | | JP | 2004-518102 | 6/2004 |
| FR | 2 752 242 | 2/1998 | | JP | 2004-216246 | 8/2004 |
| FR | 2 862 644 | 5/2005 | | JP | 2005-007841 | 1/2005 |
| FR | 2 868 419 | 10/2005 | | JP | 2005-097177 | 4/2005 |
| FR | 2 869 612 | 11/2005 | | JP | 76021635 | 4/2005 |
| FR | 2 869 613 | 11/2005 | | JP | 2005-513064 | 5/2005 |
| FR | 2 872 504 | 1/2006 | | JP | 2007-008898 | 1/2007 |
| FR | 2 881 732 | 8/2006 | | JP | 2009-263338 | 11/2009 |
| FR | 2 885 903 | 11/2006 | | KR | 900006513 | 11/1987 |
| FR | 2 912 743 | 8/2008 | | KR | 2003-29740 | 5/2003 |
| FR | 2 913 683 | 9/2008 | | KR | 10-0514819 | 11/2004 |
| FR | 2 917 411 | 12/2008 | | SU | 123153 | 1/1959 |
| FR | 2 918 058 | 1/2009 | | SU | 1159716 | 6/1975 |
| FR | 2 925 045 | 6/2009 | | SU | 1125226 | 11/1984 |
| FR | 2 929 611 | 10/2009 | | SU | 1685969 | 10/1991 |
| FR | 2 935 699 | 3/2010 | | WO | WO 95/14639 | 6/1995 |
| FR | 2 935 968 | 3/2010 | | WO | WO 96/07617 | 3/1996 |
| GB | 14 767 | 0/1914 | | WO | WO 96/15980 | 5/1996 |
| GB | 404 938 | 7/1932 | | WO | WO 97/48667 | 12/1997 |
| GB | 406345 | 8/1932 | | WO | WO 98/37024 | 8/1998 |
| GB | 467 481 | 9/1935 | | WO | WO 99/14208 | 3/1999 |
| GB | 541357 | 11/1941 | | WO | WO 99/32397 | 7/1999 |
| GB | 679 536 | 9/1952 | | WO | WO 00/24674 | 5/2000 |
| GB | 736641 | 7/1953 | | WO | WO 01/41919 | 6/2001 |
| GB | 799 567 | 8/1958 | | WO | WO 01/86220 | 11/2001 |
| GB | 1046521 | 1/1964 | | WO | WO 02/26672 | 4/2002 |
| GB | 1083594 | 11/1964 | | WO | WO 02/059536 | 8/2002 |
| GB | 984446 | 2/1965 | | WO | WO 03/064357 | 8/2003 |
| GB | 984 633 | 3/1965 | | WO | WO 2004/056758 | 7/2004 |
| GB | 1 387 668 | 3/1972 | | WO | WO 2005/024176 | 3/2005 |
| GB | 1286893 | 8/1972 | | WO | WO 2005/054167 | 6/2005 |
| GB | 1 493 538 | 4/1975 | | WO | WO 2005/097722 | 10/2005 |
| GB | 1 414 976 | 11/1975 | | WO | WO 2005/115954 | 12/2005 |
| GB | 2 173 496 | 10/1986 | | WO | WO 2005/116004 | 12/2005 |
| GB | 702143 | 10/1990 | | WO | WO 2006/020234 | 2/2006 |
| GB | 2 336 584 | 10/1999 | | WO | WO 2006/100311 | 9/2006 |
| HU | 2002-003023 | 3/2004 | | WO | WO 2006/100312 | 9/2006 |
| JP | 39-27230 | 11/1928 | | WO | WO 2006/100313 | 9/2006 |
| JP | 50-062909 | 5/1975 | | WO | WO 2006/100314 | 9/2006 |
| JP | 55-041858 | 3/1980 | | WO | WO 2006/100315 | 9/2006 |
| JP | 56-29572 | 3/1981 | | WO | WO 2006/100316 | 9/2006 |
| JP | 56-99432 | 8/1981 | | WO | WO 2006/100317 | 9/2006 |
| JP | 56-155009 | 12/1981 | | WO | WO 2006/100318 | 9/2006 |
| JP | 60-258171 | 12/1985 | | WO | WO 2006/100319 | 9/2006 |

| WO | WO 2006/100320 | 9/2006 |
| --- | --- | --- |
| WO | WO 2006/106153 | 10/2006 |
| WO | WO 2006/106154 | 10/2006 |
| WO | WO 2006/106155 | 10/2006 |
| WO | WO 2007/05405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/026212 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

U.S. Appl. No. 11/915,059, filed Nov. 20, 2007, Gilbeau, et al.
U.S. Appl. No. 11/914,836, filed Nov. 19, 2007, Krafft, et al.
U.S. Appl. No. 11/915,067, filed Nov. 20, 2007, Krafft, et al.
U.S. Appl. No. 11/914,874, filed Nov. 19, 2007, Krafft, et al.
U.S. Appl. No. 11/914,862, filed Nov. 19, 2007, Gilbeau.
U.S. Appl. No. 11/914,856, filed Nov. 19, 2007, Krafft, et al.
U.S. Appl. No. 11/914,868, filed Nov. 19, 2007, Krafft.
U.S. Appl. No. 11/915,046, filed Nov. 20, 2007, Krafft, et al.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 60/560,676, filed Apr. 8, 2004, Un Known.
U.S. Appl. No. 60/734,659, filed Nov. 8, 2005, Un Known.
U.S. Appl. No. 60/734,627, filed Nov. 8, 2005, Un Known.
U.S. Appl. No. 60/734,657, filed Nov. 8, 2005, Un Known.
U.S. Appl. No. 60/734,658, filed Nov. 8, 2005, Un Known.
U.S. Appl. No. 60/734,635, filed Nov. 8, 2005, Un Known.
U.S. Appl. No. 60/734,634, filed Nov. 8, 2005, Un Known.
U.S. Appl. No. 60/734,637, filed Nov. 8, 2005, Un Known.
U.S. Appl. No. 60/734,636, filed Nov. 8, 2005, Un Known.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Un Known.
Semendyava, N.D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy 1 Ikh Primenenie (1988), 4, 69-71 (CA Summary) XP 002465276.
Kirk Othmer Encyclopedia of Chemical Technology, Third Edition, vol. 12, 1980, pp. 1002-1005.
Chemical Engineering Handbook, the 6$^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Herman A. Bruson, et al., "Thermal Decomposition of Glyceryl Carbonates," Journal of the American Chemical Society, vol. 74, Apr. 1952 pp. 2100-2101.
Catalogue of Nittetu Chemical Engineering Ltd. (Published in Mar. 1994).
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and similar passages but retrieved from the English 5$^{th}$ Edition of the Book, 1987.
Perry's Chemical Engineers Handbook 7$^{th}$ Ed. 11$^{th}$ Section, 1997.
Perry's Chemical Engineers Handbook 7$^{th}$ Ed. 13$^{th}$ Section, 1997.
Perry's Chemical Engineers Handbook 7$^{th}$ Ed. 15$^{th}$ Section, 1997.
Ullmann Encyclopedia Industr. Chem. 5$^{th}$ Ed., vol. A23, 1993 pp. 635-636.
Ullmann Encyclopedia Industr. Chem. 5$^{th}$ Ed., vol. A13, 1989 pp. 289.
Ullmann Encyclopedia Industr. Chem. 5$^{th}$ Ed., vol. A11, 1988 pp. 354-360.
U.S. Appl. No. 12/304,391, filed Dec. 11, 2008, Krafft, et al.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- and Wassermengenwirtschaft e; V;—2005 p. 81/-8/5., vol. 5.
Klaus Weissermel, et al., "Industrial Organic Chemistry," (3$^{rd}$ Completely Revised Edition); VCH 1997. p. 93-98.
Klaus Weissermel, et al., "Industrial Organic Chemistry," (3$^{rd}$ Completely Revised Edition); VCH 1997. p. 276-277.
Klaus Weissermel, et al., "Industrial Organic Chemistry," (3$^{rd}$ Completely Revised Edition); VCH 1997. p. 347-355.
U.S. Appl. No. 12/502,296, filed Jul. 14, 2009, Krafft, et al.
U.S. Appl. No. 12/502,342, filed Jul. 14, 2009, Krafft, et al.
U.S. Appl. No. 12/527,538, filed Aug. 17, 2009, Gilbeau, et al.
U.S. Appl. No. 12/529,777, filed Sep. 3, 2009, Krafft, et al.
U.S. Appl. No. 12/529,778, filed Sep. 3, 2009, Krafft, et al.
M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.
U.S. Appl. No. 12/600,018, filed Nov. 13, 2009, Borremans, et al.
U.S. Appl. No. 12/663,753, filed Dec. 9, 2009, Krafft, et al.
U.S. Appl. No. 12/663,744, filed Dec. 9, 2009, Boulos, et al.
U.S. Appl. No. 12/663,749, filed Dec. 9, 2009, Krafft, et al.
U.S. Appl. No. 12/663,887, filed Dec. 10, 2009, Krafft, et al.
U.S. Appl. No. 12/681,083, filed Mar. 31, 2010, Bobet, et al.
RD 436093, Aug. 10, 2000, Research Disclosure.
Ullmann's Encyclopedia of Industrial Chemistry, 2005, Wiley-VCH GmbH & Co., KgaA, Weinhem, pp. 8-15 and 401-477, Published online Mar. 15, 2001.
U.S. Appl. No. 12/864,211, filed Jul. 27, 2010, Gilbeau, et al.
U.S. Appl. No. 13/238,206, filed Sep. 21, 2011, Gilbeau, et al.
Production and Prospect of the World Natural Glycerol by Zhu Shiyong, Cereals and Oils, vol. 1, 1997, pp. 33-38 (No English Translation).
Vinnolit; Vinnolit receives EU grant for water recycling project; Press Rlease, 2008: http://www.vinnolit.de/vinnolit.nfs/id/EN_Vinnolit_receives_EU$_{13}$grant_for_water_recycling_project_.
N.W. Ziels, Journal of American Oil Chemists' Society, Nov. 1956, vol. 33, pp. 556-565.
U.S. Appl. No. 13/060,421, filed Feb. 23, 2011, Balthasart, et al.
W. Giger et al., "14C/12C—Ratios in Organic Matter and Hydrocarbons Extracted from Dated Lake Sediments," Nuclear Instruments and Methods in Physics Research B5 (1984), 394-397. XP002631954.

Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661, XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

U.S. Appl. No. 13/131,516, filed May 26, 2011, Gilbeau, et al.

Azeotropic Data-III Complied by Lee H. Horsley, The Dow Chemical Co., Midland, Mich., American Chemical Society (1973).

Yoshikazu Suzawa et al., Kagachu Sohchi (Chemical Apparatuses), vol. 23, No. 11, 3744, (published on Nov. 1981) with English translation.

Journal of American Oil Chemists' Society Jul. 1982, vol. 59, No. 7 pp. 292-295.

Chemical Engineering Handbook, 6th Revised Edition, 2nd print issued on Apr. 25, 2001, with attached English translation.

Organic synthesis, Part 1, published by Scientific Publishing, 1957.

Handbook of chemical products, organic chemical materials, Second edition, published by Chemical Industry Press, Jan. 1995.

R. A. Kiseleva and V.M. Goncharko, J. Appl. Chem. USSR, 1971, vol. 44, pp. 2086-2090.

Handbook of Corrosion data and material selection, published by Chemical Industry Press, edited by Jingyi Zuo, Yu Zuo, first edition, Oct. 1995 with attached English Translation.

Handbook of azeotropic mixture, edited by information department of comprehensive scientific technology research institution of Fushun City, 1993.

Industry chemical reaction and application, published by Chinese Scientific Technology University Press, 1999 with attached English translation.

Epoxy resin, published by Shanghai People's Publishing House, 1971, with attached English Translation.

Boschan and S. Winstein, Journal of the American Chemical Society, 1956, vol. 78, pp. 4921-4925.

Encyclopedia for Chinese Adult Education, 1994, p. 623.

"Electrolytic cell test for electrolysis of epoxy sewage salt to prepare chlor-alkali", process Equipment Department of Research Institute of chlor-alkali, Shengyang chemical Plant, Liaononhg Chemical Industry, Issue No. 2, pp. 32-37, published Dec. 31, 1981, with attached English translation.

"Analysis of the Composition of the Byproduct During the Manufacturing Process of Sepichlorhydrin by GC-MS", Ren Chengxin et al., Chemical Analysis and Measurement, vol. 12, Issue No. 3, p. 25-26, Dec. 31, 2003, with attached English translation.

Encyclopedia of Chemical Technology, vol. 5, Nov. 1993.

Manufacture and use of epoxy resin, edited by Shanghai Resin Factory, published by China Petrochemical Press, First Edition, Oct. 1974.

Perry's Chemical Engineers Handbook, Sixth Edition, McGraw Hill Inc. (1984) Section 18. vol. B3, Unit Operations II of Ullmann's Encyclopedia of Industial Chemistry, Fifth Completely Revised Edition, Published by VCH, 1988.

U.S. Appl. No. 13/051,007, filed Mar. 18, 2011, Krafft, et al.

U.S. Appl. No. 13/063,230, filed Mar. 10, 2011, Krafft, et al.

Ma Zengxin, Gan Yicui, Recovery of Polyglycerol from Residues of Synthetic Glycerol—Riyong Huaxue Gongye, 1997, 4, 21023 (Abstract Only).

U.S. Appl. No. 12/935,538, filed Sep. 29, 2010, Gilbeau, et al.

Myszkowski J. et al., "Removal of Chlorinated Organic Impurities from Hydrogen Chloride," CA, Jan. 1, 1990, XP002352444 (English CA Summary only).

Myszkowski J. et al., "Removal of Organic Compoiunds from Gaseous Hydrogen Chloride by an Absorption Method," CA, Jan. 1, 1900, XP002352445 (English CA summary only).

Milchert E. et al., "Recovering Hydrogen Chloride and Organic Chlor Compounds from the Reaction Mixture in the Chlorination of Ethylene," CA, Jan. 1, 1990, XP002352443 (English CA Summary only).

Laine D.F., et al., "The Destruction of Organic Pollutants Under Mid Reaction Conditions ; A Reveiw," Microchemical Journal, vol. 85, No. 2, 2006, pp. 183-193.

Rainwater Harvesting and Utilization, Internet Citation, XP003003726, Mar. 2002.

H. Galeman, Organic Synthesis, Section 1, p. 234-235, 1941.

Chemical Encyclopedia 5, p. 457, 1996.

Epoxy Resins, Shanghai Resin Plant, Shangai Peoples's Press, 1971.

Martinetti Richard et al., "Environment Le Recyclage De l'eau," Industrie Textile, Ste. Sippe Sarl, Metz, FR., No. 1300, Jul. 1, 1998 ISSN: 0019-9176.

Fauconnier, "Preparation of Epichlorohydrin," Bull. Soc. Chim. Fr., No. 122, pp. 212-214 (with English Translation), 1884.

U.S. Appl. No. 12/745,802, filed Jun. 2, 2010, Gilbeau, et al.

New Experimental Chemical Course 1, Basic Operation I. Section 4, Separation and Purification, pp. 251-252, Issued Sep. 20, 1975 (with English Translation).

Copyright Mar. 1992, Advanced Organic Chemistry, $4^{th}$ Ed., pp. 889, 908, 937.

Yong, K.C., et al., "Refining of Crude Glycerine Recovered from Glycerol Residue by Simple Vacuum Distillation," Journal of Oil Palm Research, vol. 13, No. 2, Dec. 2001, pp. 39-44.

Friedel et Silva, Bulletin de la Société Chimique de Paris, Année 1873, 1er semestre—Nouvelle Série—Tome XIX, p. 98.

I.S. Neuberg, Biochemische Zeitshrift, 1930, vol. 221, pp. 492-493.

F. Krausz Ann. De Chimie, 12e série, t. 4 Nov.-Dec. 1949, pp. 811-931.

Glycerin : An overview, Soap and Detergent Assocation. Copyright 1990 by the Soap and Detergent Association.

Chemical and Engineering News, 1948, 26 (38), pp. 2770-2771.

Fairbourn et al., "The Partial Esterification of Polyhydric Alcohols. Part XII. The Function of Ethylene-oxide Rings," J. Chem. Soc. 1932, pp. 1965-1972.

Clarke et al., Organic Synthesis, Coll., vol. 1, p. 233, (1941); vol. 3, p. 47, (1923).

Braun, Organic Synthesis, Coll., vol. 2, p. 256, (1943); vol. 6, p. 30, (1936).

Conant et al. Organic Syntheses, Coll., vol. 1, p. 292, (1941); vol. 2, p. 29, (1992).

Bull. Soc. Chim. Fr. (1943), 10, pp. 52-58, with English Translation.

Schröder et al. "Glycerol as a By-Product of Biodiesel Producton in Diets for Ruminants," Institute of Animal Nutrition, Physiology and Metabolism, University of Kiel, 24098 Kiel, 1999.

"Chemical Properties of Derivatives of Glycerol", (1965), published by Glycerine Producers' Association in New York. pp. 1-20.

G.W. Busby and D.E. Gosvenor, "The Purification of Glycerin by Ion-Exchange," The Journal of The American Oil Chemists' Society, vol. 29, No. 8, pp. 318-320 (1952).

L.L. Lamborn, "Modern Soaps, Candles and Glycerin," D. Van NOstrand Company, London, third edition, 1918, pp. 542-550, 573-574.

G. Knothe, "Historical perspectives on vegtable oil-based diesel fuels", Inform, vol. 12, Nov. 2001, pp. 1103-1107.

U. Schuchardt et al., "Transesterification of Vegetable Oils: a Review," J. Braz. Chem. Soc., vol. 9, No. 1, 199-210, 1998.

S. Claude, "Research of new outlets for glycerol—recent developments in France," Fett/Lipid 101 (1999), Nr. 3, S 101-104.

C.B. Prakash,"A critical review of Biodiesel as a Transportation Fuel in Canada," for the Transportation Systems Branch Air Pollution Prevention Directorate Environment Canada, Mar. 25, 1998, pp. 1-104.

H. Fukuda et al., "Biodiesel Fuel Production by transesterification of Oils", Journal of Bioscience and Bioengineering, vol. 92, No. 5, pp. 405-416 (2001).

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

Ullmann Encyl. Industr. Chem., $5^{th}$ Ed., vol. A6, (1988), pp. 401-477.

Polymer Science Dictionary, M.S.M., Elsevier Applied Chemistry, London and New York, 1989, p. 86.

Perry's chemical Engineers' Handbook, Sixth Edition, Section 21, pp. 21-55, 1973.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

Encyclopedia of Experimental Chemistry I, Basic Operation I, edited by The Chemcial Society of Japan, Maruzen Co., Ltd., Nov. 5, 1990, 4th Edition, pp. 161 to 165 and 184 to 191 (no English translation available.

Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312-313 (no English translation available).

Clarke et al., Org. Synth., Coll. vol. 1, p. 233-234, 1964.

Braun, Org. Synth., Coll., vol. 2, p. 256-259, 1957.

Kirk Othmer Encyclopedia of Chemical Technology, 3rd Edition, vol. 9, pp. 267-289, 1980.

Armandro Novelli, "The Preparation of Moni- and Dichlorohydrins of Glycerol," Anal. Farm. Bioquim, vol. 1, 1930, pp. 8-19 (with English Abstract).

Derwent Publications, AN 109:6092 CA, JP 62-242638 (Oct. 23, 1987).

Derwent Publications, AN 1987-338139 [48], JP 62-242638, (Oct. 23, 1987).

Kirk-Othmer Encyclopedia of Chemical Technology, Third Edition, vol. 4, Blood, Coagulants and Anticoagulants to Cardiovascular Agents, 1978.

J.B. Conant et al., "Glycerol a.y-Dichlorophydrin," Organic Syntheses Coll., vol. 1, p. 292, 1941.

I. Miyakawa et al., Nagoya Sangyo Kagaku Kenkyusho Kenkyu Hokoku, 10, 49-52 (1957).

Han Xiu-Ying et al., Shanxi Daxue Xueba Bianjibu, 2002, 25(4), 379-80).

Gibson., "The Preparation, Properties, and Uses of Glycerol Derivatives, Part III. The Chlorohydrins", Chemistry and Industry, Chemical Society, pp. 949-975, 1931.

Carrie et al., "La Transformation des Alcools Polyatomiques en Mono-Et en Polychlorhydrines au Moyen du Chlorure de Thionyle", Bull. Soc. Chim. FR., No. 49, pp. 1150-1154, 1931.

Fauconnier, "Preparation de L'Epichlorhydrine", Bull. Soc. Chim. FR., No. 50, pp. 212-214, 1888.

"Industrially Important Epoxides", Ullmann's Encyclopedia of Industrial Chemistry, 5.ed, vol. A9, pp. 539-540, 1987.

Bonner et al., "The Composition of Constant Boiling Hydrochloric Acid at Pressures of 50 to 1220 Millimeters", Journal of American Chemical Society, vol. 52, pp. 633-635, 1930.

Muskopf et al., "Epoxy Resins", Ullmann's Encyclopedia of Industrial Chemistry, 5.ed, vol. A9, pp. 547-562, 1987.

Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870, 1999.

Oleoline, com, Glycerine Market report, Sep. 10, 2003, No. 62.

Notification Under Act. No. 100/2001, Coll. as Amended by Act No. 93/2004, Coll. to the extent of Annex No. 4, (SPOLEK) Nov. 30, 2004.

Documentation Under Act No. 100/2001 Coll. as amended by Act No. 93/2004 Coll in the scope of apendix No. 4 (SPOLEK) Jan. 11, 2005.

K. Weissemel and H J. Arpe in Industrial Organic Chemistry, Third, Completely Revised Edition, VCH, 1997, pp. 149,275.

Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & Sons, Inc.

Ullman's Encyclopedia of Industrial Chemistry, Fifth, Completely Revised Edition, 1985, vol. A13, pp. 292-293.

The Merck Index, Eleventh Edition, 1989, pp. 759-760.

Ullmann's Encyclopedia of Industrial Chemistry, Fifth Completely Revised Edition, vol. A1, pp. 427-429, 1985.

Ullmann's Encyclopedia of Industrial Chemistry, Fifth Completely REvised Edition, vol. A6, pp. 240-252, 1986.

Hancock, E.G., Propylene and its Industrial Derivatives, 1973, pp. 298-332.

K. Weissermel and H. J. Arpe in Industrial Organic Chemistry, Third, Completely Revised Edition, VCH 1997, pp. 149-163.

K. Weissermel and H. J. Arpe in Industrial Organic Chemistry, Third Completely Revised Edition, VCH 1997, pp. 275-276.

Ullmann's Encyclopedia of Industrial Chemistry, Fifth Completely Revised Edition, vol. A9, pp. 539-540, 1987.

Perry's Chemical Engineers Handbook, Sixth Edition, Robert H. Perry, Don Green, 1984, Section 21-44 to 21-68

Iwanami Dictionary of Physics and Chemistry, Third edition, Ryo Midorikawa/Iwanami Shoten, Publishers, May 29, 1971, pp. 270-271, 595 amd 726.

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.

* cited by examiner

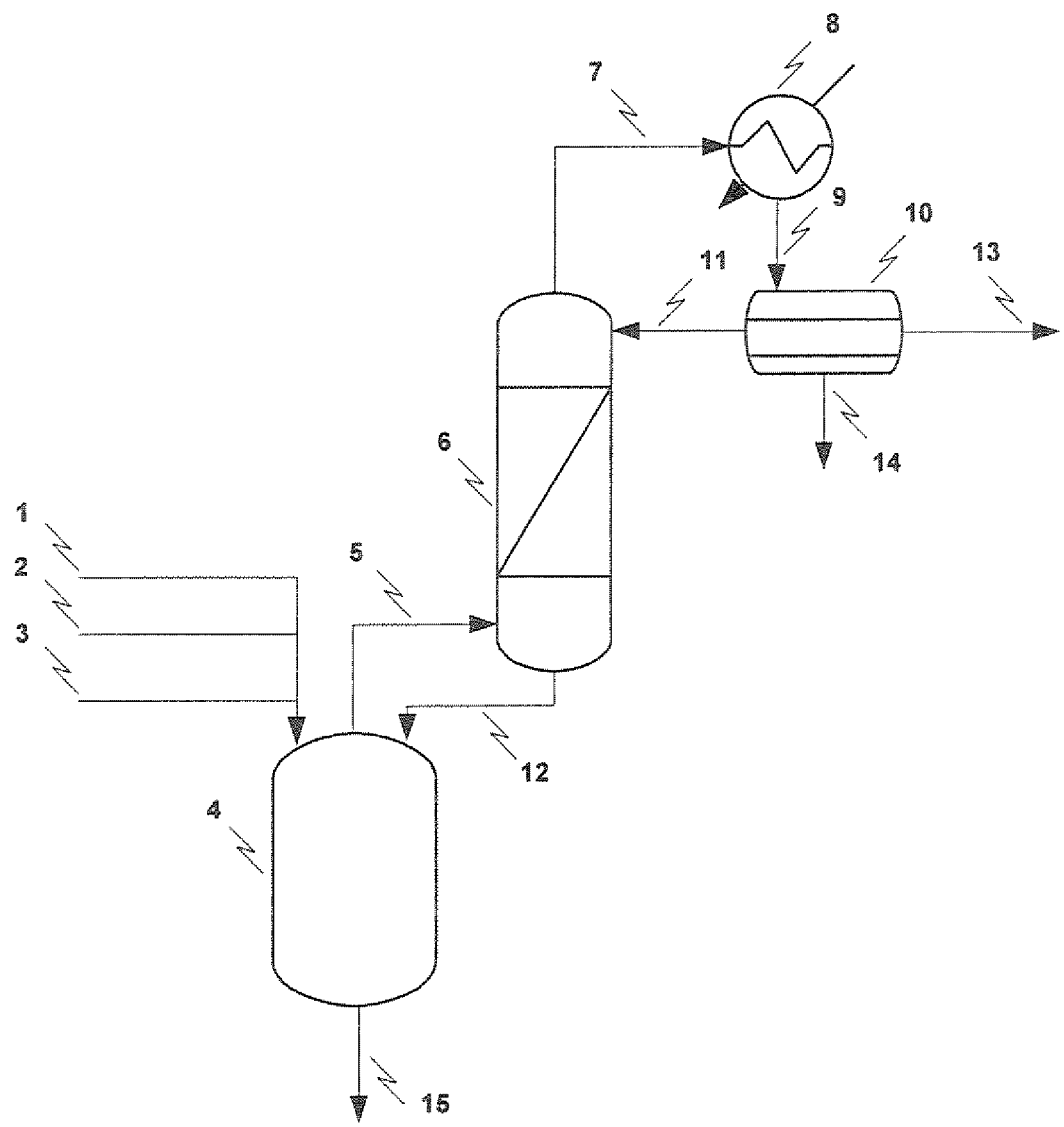

CONTINUOUS METHOD FOR MAKING CHLORHYDRINES

The present patent application is a 371 of PCT/EP06/62463, filed May 19, 2006. The present patent application also claims the benefit of patent application FR 05.05120 and of patent application EP 05104321.4, both filed on 20 May 2005, and of provisional U.S. patent applications 60/734,659, 60/734,627, 60/734,657, 60/734,658, 60/734,635, 60/734,634, 60/734,637 and 60/734,636, all filed on 8 Nov. 2005, the content of all of which is incorporated here by reference.

The present invention relates to a continuous process for preparing a chlorohydrin.

Chlorohydrins are reaction intermediates in the preparation of epoxides. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

International application WO 2006/020234 describes a process for converting a polyhydroxylated aliphatic hydrocarbon or an ester thereof into a chlorohydrin. A composition is disclosed that comprises not more than 1% of the polyhydroxylated aliphatic hydrocarbon and esters of the polyhydroxylated aliphatic hydrocarbon. This composition is characteristic of a process not suitable for continuous operation.

The objective of the invention is to provide a continuous process for producing a chlorohydrin that does not exhibit these drawbacks.

The invention accordingly provides a continuous process for producing chlorohydrin in which a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition comprises polyhydroxylated aliphatic hydrocarbon and esters of polyhydroxylated aliphatic hydrocarbon for which the sum of the amounts, expressed in moles of polyhydroxylated aliphatic hydrocarbon, is greater than 1.1 mol % and less than or equal to 30 mol %, the percentage being based on the organic part of the liquid reaction medium.

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol(ethylene glycol), 1,2-propanediol(propylene glycol), 1,3-propanediol, 1-chloro-2,3-propanediol(chloropropanediol), 2-chloro-1,3-propanediol(chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of the polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon. Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

In the process for producing a chlorohydrin according to the invention, the organic acid may be a product originating from the process for preparing the polyhydroxylated aliphatic hydrocarbon, i.e. an impurity contained in the polyhydroxylated aliphatic hydrocarbon, or a product not originating from this process. In this latter case the product in question may be an organic acid which is used in order to catalyse the reaction of the polyhydroxylated aliphatic hydrocarbon with the chlorinating agent. The organic acid may also be a mixture of an organic acid originating from the process for preparing the polyhydroxylated aliphatic hydrocarbon, and of an organic acid not originating from the process for preparing the polyhydroxylated aliphatic hydrocarbon.

In the process according to the invention, the esters of the polyhydroxylated aliphatic hydrocarbon may originate from the reaction between the polyhydroxylated aliphatic hydrocarbon and the organic acid, before, during or within the steps which follow the reaction with the chlorinating agent.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used in the process of the invention, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

In the process for producing a chlorohydrin according to the invention, the polyhydroxylated aliphatic hydrocarbon, the ester of polyhydroxylated aliphatic hydrocarbon or the mixture thereof may be as described in the patent application entitled "Process for preparing chlorohydrin by converting polyhydroxylated aliphatic hydrocarbons", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of a polyhydroxylated aliphatic hydrocarbon or a mixture thereof whose total metal content, expressed in elemental form, is greater than or equal to 0.1 µg/kg and less than or equal to 1000 mg/kg is reacted with a chlorinating agent.

In the process for producing a chlorohydrin according to the invention, the polyhydroxylated aliphatic hydrocarbon, the ester of polyhydroxylated aliphatic hydrocarbon or the mixture thereof may be a crude product or a purified product, such as are specifically disclosed in application WO 2005/054167 of SOLVAY SA, from page 2 line 8 to page 4 line 2.

In the process for producing a chlorohydrin according to the invention, the polyhydroxylated aliphatic hydrocarbon, the ester of polyhydroxylated aliphatic hydrocarbon or the mixture thereof may have an alkali metal and/or alkaline earth metal content of less than or equal to 5 g/kg, as described in the application entitled "Process for preparing a chlorohydrin by chlorinating a polyhydroxylated aliphatic hydrocarbon", filed in the name of SOLVAY SA on the same day as the present application, and whose content is incorporated here by reference. The alkali metals may be selected from lithium, sodium, potassium, rubidium and cesium and the alkaline earth metals may be selected from magnesium, calcium, strontium and barium.

In the process according to the invention, the alkali metal and/or alkaline earth metal content of the polyhydroxylated aliphatic hydrocarbon, the ester of polyhydroxylated aliphatic hydrocarbon or the mixture thereof is less than or equal to 5 g/kg, often less than or equal to 1 g/kg, more particularly less than or equal to 0.5 g/kg and in certain cases less than or equal to 0.01 g/kg. The alkali metal and/or alkaline earth metal content of the glycerol is generally greater than or equal to 0.1 µg/kg.

In the process according to the invention the alkali metals are generally lithium, sodium, potassium and cesium, often sodium and potassium, and frequently sodium.

In the process for preparing a chlorohydrin according to the invention, the lithium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the sodium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the potassium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the rubidium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the cesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkaline earth metal elements are generally magnesium, calcium, strontium and barium, often magnesium and calcium and frequently calcium.

In the process according to the invention, the magnesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the calcium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the strontium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the barium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention the alkali and/or alkaline earth metals are generally present in the form of salts, frequently in the form of chlorides, sulphates and mixtures thereof. Sodium chloride is the most often encountered.

In the process for producing a chlorohydrin according to the invention, the chlorinating agent may be as described in application WO 2005/054167 of SOLVAY SA, from page 4 line 25 to page 6 line 2.

In the process for producing a chlorohydrin according to the invention, the chlorinating agent may be hydrogen chloride perhaps as described in application WO 2005/054167 of SOLVAY SA, from page 4 line 30 to page 6 line 2.

Particular mention is made of a chlorinating agent which may be aqueous hydrochloric acid or hydrogen chloride which is preferably anhydrous.

The hydrogen chloride may originate from a process for pyrolysing organic chlorine compounds, such as, for example, from a vinyl chloride production, from a process for producing 4,4-methylenediphenyl diisocyanate (MDI) or toluene diisocyanate (TDI), from metal pickling processes or from the reaction of an inorganic acid such as sulphuric or phosphoric acid with a metal chloride such as sodium chloride, potassium chloride or calcium chloride.

In one advantageous embodiment of the process for producing a chlorohydrin according to the invention, the chlorinating agent is gaseous hydrogen chloride or an aqueous solution of hydrogen chloride, or a combination of the two.

In the process for producing a chlorohydrin according to the invention, the hydrogen chloride may be an aqueous solution of hydrogen chloride or may be preferably gaseous hydrogen chloride, obtained from a plant for producing allyl chloride and/or for producing chloromethanes and/or a chlorinolysis plant and/or a plant for high-temperature oxidation of chlorine compounds, as described in the application entitled "Process for preparing a chlorohydrin by reacting a polyhydroxylated aliphatic hydrocarbon with a chlorinating agent", filed in the name of SOLVAY SA on the same day as the present application, and the content of which is incorporated here by reference.

Particular mention is made of a process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

Particular mention is made of an organic hydrocarbon compound which is selected from saturated or unsaturated aliphatic and aromatic hydrocarbons and mixtures thereof.

Particular mention is made of an unsaturated aliphatic hydrocarbon which is selected from acetylene, ethylene, propylene, butene, propadiene, methylacetylene and mixtures thereof, of a saturated aliphatic hydrocarbon which is selected from methane, ethane, propane, butane and mixtures thereof and of an aromatic hydrocarbon which is benzene.

Particular mention is made of an organic halogen compound which is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

Particular mention is made of an organic halogen compound which is an organic fluorine compound selected from fluoromethanes, fluoroethanes, vinyl fluoride, vinylidene fluoride and mixtures thereof.

Particular mention is made of an organic oxygen compound which is selected from alcohols, chloroalcohols, chloroethers and mixtures thereof.

Particular mention is made of a metal selected from alkali metals, alkaline earth metals, iron, nickel, copper, lead, arsenic, cobalt, titanium, cadmium, antimony, mercury, zinc, selenium, aluminium, bismuth and mixtures thereof.

Mention is made more particularly of a process wherein the chlorinating agent is obtained at least partly from a process for preparing allyl chloride and/or a process for preparing chloromethanes and/or a process of chlorinolysis and/or a process for oxidizing chlorine compounds at a temperature greater than or equal to 800° C.

In one particularly advantageous embodiment of the production process according to the invention, the hydrogen chloride is an aqueous solution of hydrogen chloride and does not contain gaseous hydrogen chloride.

In the process for producing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reactor as described in application WO 2005/054167 of SOLVAY SA on page 6 lines 3 to 23.

Mention is made particularly of a plant made of or covered with materials which are resistant, under the reaction conditions, to the chlorinating agents, particularly to hydrogen chloride. Mention is made more particularly of a plant made of enamelled steel or of tantalum.

In the process for producing a chlorohydrin according to the invention, the reaction of the polyhydroxylated aliphatic hydrocarbon, the ester of the polyhydroxylated aliphatic hydrocarbon or the mixture thereof with the chlorinating agent may be carried out in apparatus which is made of or covered with materials that are resistant to chlorinating agents, as described in the patent application entitled "Process for preparing a chlorohydrin in corrosion-resistant apparatus", filed in the name of SOLVAY SA on the same day as the present application, and the content of which is incorporated here by reference.

Particular mention is made of a process for preparing a chlorohydrin that includes a step in which a polyhydroxylated aliphatic hydrocarbon, an ester of a polyhydroxylated aliphatic hydrocarbon or a mixture thereof is subjected to reaction with a chlorinating agent containing hydrogen chloride and to at least one other step carried out in an apparatus made of or covered with materials resistant to the chlorinating agent, under the conditions in which that step is realized. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and unimpregnated and impregnated graphite.

In the process for producing a chlorohydrin according to the invention, the reaction of the polyhydroxylated aliphatic hydrocarbon, the ester of polyhydroxylated aliphatic hydrocarbon or the mixture thereof and the chlorinating agent may be carried out in the presence of a catalyst as described in application WO 2005/054167 of SOLVAY SA from page 6 line 28 to page 8 line 5.

Mention is made particularly of a catalyst based on a carboxylic acid or on a carboxylic acid derivative having an atmospheric boiling point of greater than or equal to 200° C., especially adipic acid and derivatives of adipic acid.

In the process for producing a chlorohydrin according to the invention, the reaction of the polyhydroxylated aliphatic hydrocarbon, the ester of polyhydroxylated aliphatic hydrocarbon or the mixture thereof and the chlorinating agent may be carried out at a catalyst concentration, temperature and pressure and for residence times as described in the application WO 2005/054167 of SOLVAY SA from page 8 line 6 to page 10 line 10.

Mention is made particularly of a temperature of at least 20° C. and not more than 160° C., of a pressure of at least 0.3 bar and not more than 100 bar and of a residence time of at least 1 h and not more than 50 h.

In the process for producing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a solvent as described in application WO 2005/054167 of SOLVAY SA at page 11 lines 12 to 36.

Mention is made particularly of organic solvents such as a chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol and mixtures of chloropropanediol and dichloropropanol, or heavy products of the reaction such as at least partially chlorinated and/or esterified oligomers of the polyhydroxylated aliphatic hydrocarbon.

In the process for producing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon and having a boiling temperature under a pressure of 1 bar absolute of at least 15° C. more than the boiling temperature of the chlorohydrin under a pressure of 1 bar absolute.

In the process for producing a chlorohydrin according to the invention the reaction of the polyhydroxylated aliphatic hydrocarbon, the ester of polyhydroxylated aliphatic hydrocarbon or the mixture thereof with the chlorinating agent is carried out in a liquid reaction medium. The liquid reaction medium may be a single-phase or multi-phase medium.

The liquid reaction medium is composed of all of the dissolved or dispersed solid compounds, dissolved or dispersed liquid compounds and dissolved or dispersed gaseous compounds at the temperature of the reaction.

The reaction medium comprises the reactants, the catalyst, the solvent, the impurities present in the reactants, in the solvent and in the catalyst, the reaction intermediates, the products and the by-products of the reaction.

By reactants are meant the polyhydroxylated aliphatic hydrocarbon, the ester of polyhydroxylated aliphatic hydrocarbon and the chlorinating agent.

Among the impurities present in the polyhydroxylated aliphatic hydrocarbon mention may be made of carboxylic acids, salts of carboxylic acids, esters of fatty acid with the polyhydroxylated aliphatic hydrocarbon, esters of fatty acids with the alcohols used in the transesterification, and inorganic salts such as alkali metal or alkaline earth metal sulphates and chlorides.

When the polyhydroxylated aliphatic hydrocarbon is glycerol, the impurities in the glycerol that may be mentioned include carboxylic acids, salts of carboxylic acids, fatty acid esters such as mono-, di- and triglycerides, esters of fatty acids with the alcohols used in the transesterification and inorganic salts such as alkali metal or alkaline earth metal sulphates and chlorides.

Among the reaction intermediates mention may be made of monochlorohydrins of the polyhydroxylated aliphatic hydrocarbon and their esters and/or polyesters, the esters and/or polyesters of the polyhydroxylated aliphatic hydrocarbon and the esters of polychlorohydrins.

When the chlorohydrin is dichloropropanol, the reaction intermediates that may be mentioned include glycerol monochlorohydrin and its esters and/or polyesters, the esters and/or polyesters of glycerol and the esters of dichloropropanol.

The ester of polyhydroxylated aliphatic hydrocarbon may therefore be, at each instance, a reactant, an impurity of the polyhydroxylated aliphatic hydrocarbon or a reaction intermediate.

By products of the reaction are meant the chlorohydrin and water. The water may be the water formed in the chlorination reaction and/or water introduced into the process, for example via the polyhydroxylated aliphatic hydrocarbon and/or the chlorinating agent, as described in the application WO 2005/054167 of SOLVAY SA at page 2 lines 22 to 28 to page 3 lines 20 to 25, at page 5 lines 7 to 31 and at page 12 lines 14 to 19.

Among the by-products mention may be made for example of the partially chlorinated and/or esterified oligomers of the polyhydroxylated aliphatic hydrocarbon.

When the polyhydroxylated aliphatic hydrocarbon is glycerol, the by-products that may be mentioned include, for example, the partially chlorinated and/or esterified oligomers of glycerol.

The reaction intermediates and the by-products may be formed in the different steps of the process, such as, for example, during the step of producing the chlorohydrin and during the steps of separating off the chlorohydrin.

The liquid reaction medium may therefore contain the polyhydroxylated aliphatic hydrocarbon, the chlorinating agent in solution or dispersion in the form of bubbles, the catalyst, the solvent, the impurities present in the reactants, the solvent and the catalyst, such as dissolved or solid salts, for example, the reaction intermediates, the products and the by-products of the reaction.

The process for preparing the chlorohydrin according to the invention is a continuous process. A continuous process generally exhibits an operating period, referred to as transitory phase, in the course of which the concentrations of the constituents of the reaction mixture change over the course of time, and then an operating period referred to as the steady state in the course of which the concentrations of the reaction mixture constituents show virtually no further change over the course of time.

In the continuous process for producing a chlorohydrin according to the invention, the liquid reaction medium has a steady-state composition which comprises the polyhydroxylated aliphatic hydrocarbon and esters of the polyhydroxylated aliphatic hydrocarbon whose sum content, expressed as moles of polyhydroxylated aliphatic hydrocarbon, is greater than 1.1 mol % and less than or equal to 30%, the percentage being based on the organic part of the liquid reaction medium.

Said sum is often greater than 2.0 mol % and frequently greater than or equal to 5 mol %. Said sum is often less than or equal to 25 mol % of the liquid reaction medium, frequently less than or equal to 15 mol % and in particular less than or equal to 10 mol %.

The organic part of the liquid reaction medium consists of all of the organic compounds of the liquid reaction medium, in other words the compounds whose molecule contains at least one carbon atom.

In the continuous process for producing a chlorohydrin according to the invention, the liquid reaction medium has a steady-state composition which comprises the chlorohydrin and chlorohydrin esters whose sum content, expressed as moles of chlorohydrin, is greater than or equal to 10 mol % and less than or equal to 98 mol %, the percentage being based on the organic part of the liquid reaction medium. Said sum is often greater than or equal to 50 mol % and frequently greater than or equal to 25 mol %. Said sum of these contents is often less than or equal to 80 mol %, frequently less than or equal to 75 mol %, in particular less than or equal to 65 mol %, and more specifically less than or equal to 55 mol %.

In the continuous process for producing a chlorohydrin according to the invention, the reaction medium has a steady-state composition which contains chlorinated oligomers of the polyhydroxylated aliphatic hydrocarbon and esters of the chlorinated oligomers of the polyhydroxylated aliphatic hydrocarbon whose sum content, expressed as moles of polyhydroxylated aliphatic hydrocarbon, is greater than or equal to 0.1 mol % and less than or equal to 20 mol %, the percentage being based on the organic part of the liquid reaction mixture. Said sum is often greater than or equal to 1 mol % and in particular greater than or equal to 5 mol %. Said sum is often less than or equal to 15 mol % of the liquid reaction medium, frequently less than or equal to 10 mol %, and in particular less than or equal to 8 mol %.

In the continuous process for producing a chlorohydrin according to the invention, the chlorohydrin may be a mixture of a monochlorohydrin and a dichlorohydrin. The chlorohydrin is preferably a mixture of monochloropropanediol and dichloropropanol.

In the continuous process for producing a chlorohydrin according to the invention, when the chlorohydrin is a mixture of monochlorohydrin and dichlorohydrin, the composition of the liquid reaction medium in the steady state contains the monochlorohydrin and monochlorohydrin esters whose sum content, expressed as moles of monochlorohydrin, is greater than or equal to 11 mol % and less than or equal to 85 mol %, the percentage being based on the organic part of the liquid reaction medium. Said sum is frequently greater than or equal to 15 mol % and in particular greater than or equal to 25 mol %. Said sum is often less than or equal to 75 mol % of the liquid reaction medium, frequently less than or equal to 60 mol % and in particular less than or equal to 45 mol %.

In the continuous process for producing a chlorohydrin according to the invention, when the chlorohydrin is a mixture of monochlorohydrin and dichlorohydrin, the composition of the liquid reaction medium in the steady state contains the dichlorohydrin and dichlorohydrin esters whose sum content, expressed as moles of dichlorohydrin, is greater than or equal to 0.5 mol % and less than or equal to 79 mol %, the percentage being based on the organic part of the liquid reaction medium. Said sum is frequently greater than or equal to 1 mol % of dichlorohydrin and esters thereof and in particular greater than or equal to 5 mol %. Said sum is often less than or equal to 55 mol % of the liquid reaction medium, frequently less than or equal to 45 mol % and in particular less than or equal to 35 mol %.

In the continuous process for producing a chlorohydrin according to the invention, the esters may originate from the reaction of the chlorohydrin, the glycerol, the chlorinated oligomers of the polyhydroxylated hydrocarbon, and the organic acid during the step of producing the chlorohydrin. The organic acid is as defined above.

The invention additionally provides a liquid composition comprising a chlorohydrin, chlorohydrin esters, a polyhydroxylated aliphatic hydrocarbon, esters of the polyhydroxylated aliphatic hydrocarbon, chlorinated oligomers of the polyhydroxylated aliphatic hydrocarbon and esters of chlorinated oligomers of the polyhydroxylated aliphatic hydrocarbon and wherein:
(a) the sum content of the polyhydroxylated aliphatic hydrocarbon and of the esters of the polyhydroxylated aliphatic hydrocarbon, expressed as moles of polyhydroxylated aliphatic hydrocarbon, in the organic part of the liquid composition is greater than 1.1 mol % and less than or equal to 30 mol % of the liquid composition
(b) the sum content of the chlorohydrin and of the chlorohydrin esters, expressed as moles of chlorohydrin, in the organic part of the liquid composition is greater than or equal to 10 mol % and less than 98 mol % of the liquid composition
(c) the sum content of the chlorinated oligomers of the polyhydroxylated aliphatic hydrocarbon and of the esters of the chlorinated oligomers of the polyhydroxylated aliphatic hydrocarbon, expressed as moles of polyhydroxylated aliphatic hydrocarbon, in the organic part of the liquid composition is greater than or equal to 0.1 mol % and less than 20 mol % of the liquid composition.

The invention additionally provides a composition comprising 1,3-dichloropropan-2-ol and 2,3-dichloropropan-1-ol and having a total 1,3-dichloropropan-2-ol and 2,3-dichloropropan-1-ol content, based on the organic part, of greater than or equal to 800 g/kg.

The organic part is defined as above.

This liquid composition may contain water and hydrogen chloride.

In the process according to the invention, the separation of the chlorohydrin and of the other compounds from the reaction mixture may be carried out in accordance with the methods as described in the application WO 2005/054167 of SOLVAY SA from page 12 line 1 to page 16 line 35 and page 18 lines 6 to 13. These other compounds are those mentioned above and include unconsumed reactants, the impurities present in the reactants, the catalyst, the solvent, the reaction intermediates, the water and the by-products of the reaction.

Particular mention is made of separation by azeotropic distillation of a water/chlorohydrin/chlorinating agent mixture under conditions which minimize the losses of chlorinating agent, followed by isolation of the chlorohydrin by decantation.

In the process for producing a chlorohydrin according to the invention, the isolation of the chlorohydrin and of the other compounds from the reaction mixture may be carried out in accordance with methods of the kind described in patent application EP 05104321.4, filed in the name of SOLVAY SA on May 20, 2005 and the content of which is incorporated here by reference. A separation method including at least one separating operation intended to remove the salt from the liquid phase is particularly preferred.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of the polyhydroxylated aliphatic hydrocarbon or a mixture thereof that is used comprises at least one solid or dissolved metal salt, the process including a separation operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of a polyhydroxylated aliphatic hydrocarbon or a mixture thereof that is used comprises at least one chloride and/or a sodium and/or potassium sulphate and in which the separating operation intended to remove part of the metal salt is a filtering operation. Particular mention is also made of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) continuously or periodically, a fraction of the reaction mixture containing at least water and the chlorohydrin is removed, (c) at least a part of the fraction obtained in step (b) is introduced into a distillation step and (d) the reflux ratio of the distillation step is controlled by providing water to the said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) continuously or periodically, a fraction of the reaction mixture containing at least water and chlorohydrin is removed, (c) at least part of the fraction obtained in step (b) is introduced into a distillation step in which the ratio between the hydrogen chloride concentration and the water concentration in the fraction introduced into the distillation step is smaller than the hydrogen chloride/water concentration ratio in the binary azeotropic hydrogen chloride/water composition at the distillation temperature and pressure.

In the process for preparing a chlorohydrin according to the invention, the separation of the chlorohydrin and of the other compounds from the reaction mixture from chlorination of the polyhydroxylated aliphatic hydrocarbon may be carried out in accordance with methods as described in the application entitled "Process for preparing a chlorohydrin", filed in the name of SOLVAY SA on the same day as the present application, and the content of which is incorporated here by reference.

Particular mention is made of a process for preparing a chlorohydrin which comprises the following steps: (a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin, (b) at least part of the mixture obtained in (a) is subjected to one or more treatments subsequent to step (a), and (c) the polyhydroxylated aliphatic hydrocarbon is added to at least one of the steps subsequent to step (a), in order to react at a temperature greater than or equal to 20° C. with the esters of the chlorohydrin, so as to form, at least partly, esters of the polyhydroxylated aliphatic hydrocarbon. Mention is made more particularly of a process in which the polyhydroxylated aliphatic hydrocarbon is glycerol and the chlorohydrin is dichloropropanol.

In the process for preparing a chlorohydrin according to the invention, the separation of the chlorohydrin and the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for preparing a chlorohydrin starting from a polyhydroxylated aliphatic hydrocarbon", filed in the name of SOLVAY SA on the same day as the present application, and the content of which is incorporated here by reference.

Particular mention is made of a process for preparing chlorohydrin by reacting a polyhydroxylated aliphatic hydrocarbon, an ester of a polyhydroxylated aliphatic hydrocarbon or a mixture thereof with a chlorinating agent in a reactor which is supplied with one or more liquid streams containing less than 50% by weight of the polyhydroxylated aliphatic hydrocarbon, of the ester of polyhydroxylated aliphatic hydrocarbon or of the mixture thereof relative to the weight of the entirety of the liquid streams introduced into the reactor. More particular mention is made of a process comprising the following steps: (a) a polyhydroxylated aliphatic hydrocarbon, an ester of a polyhydroxylated aliphatic hydrocarbon or a mixture thereof is reacted with a chlorinating agent so as to give at least one mixture containing the chlorohydrin, water and the chlorinating agent, (b) at least a fraction of the mixture formed in step (a) is removed, and (c) the fraction removed in step (b) is subjected to an operation of distillation and/or stripping wherein the polyhydroxylated aliphatic hydrocarbon is added in order to isolate, from the fraction removed in step (b), a mixture containing water and the chlorohydrin and exhibiting a reduced chlorinating agent content as compared with the fraction removed in step (b).

In the process for preparing a chlorohydrin according to the invention, the separation of the chlorohydrin and of the other compounds from the reaction mixture from chlorination of the polyhydroxylated aliphatic hydrocarbon, the ester of polyhydroxylated aliphatic hydrocarbon or the mixture thereof may be carried out in accordance with methods as described in the application entitled "Process for converting polyhydroxylated aliphatic hydrocarbons into chlorohydrins", filed in the name of SOLVAY SA on the same day as the present application, and the content of which is incorporated here by reference. Particular mention is made of a process for preparing a chlorohydrin that comprises the following steps:

(a) A polyhydroxylated aliphatic hydrocarbon, an ester of a polyhydroxylated aliphatic hydrocarbon or a mixture thereof is reacted with a chlorinating agent so as to give a mixture containing the chlorohydrin, chlorohydrin esters and water.
(b) At least a fraction of the mixture obtained in step (a) is subjected to a distillation and/or stripping treatment so as to give a portion concentrated in water, in chlorohydrin and in chlorohydrin esters.
(c) At least a fraction of the portion obtained in step (b) is subjected to a separating operation in the presence of at least one additive so as to obtain a moiety concentrated in chlorohydrin and in chlorohydrin esters and containing less than 40% by weight of water.

The separating operation is more particularly a decantation.

In the process for producing the chlorohydrin according to the invention, the isolation and the treatment of the other compounds of the reaction mixture may be carried out in accordance with methods as described in the application entitled "Process for preparing a chlorohydrin by chlorinating a polyhydroxylated aliphatic hydrocarbon", filed in the name of SOLVAY SA on the same day as the present application. A preferred treatment consists in subjecting a fraction of the by-products of the reaction to a high-temperature oxidation.

Particular mention is made of a process for preparing a chlorohydrin that comprises the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, a chlorinating agent and an organic acid are reacted so as to give a mixture containing at least the chlorohydrin and by-products, (b) at least a portion of the mixture obtained in step (a) is subjected to one or more treatments in steps subsequent to step (a), and (c) at least one of the steps subsequent to step (a) consists in an oxidation at a temperature greater than or equal to 800° C. More particular mention is made of a process wherein, in the subsequent step, a portion of the mixture obtained in step (a) is removed and this portion is subjected to oxidation at a temperature greater than or equal to 800° C. in the course of the removal. Particular mention is also made of a process wherein the treatment of step (b) is a separating operation selected from phase separation, filtration, centrifugation, extraction, washing, evaporation, stripping, distillation, and adsorption operations or the combinations of at least two of these operations.

In the process according to the invention, when the chlorohydrin is monochloropropanol, it is generally obtained in the form of a mixture of compounds comprising the isomers of 1-chloropropan-2-ol and 2-chloropropan-1-ol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanol, such as residual reactants, reaction by-products, solvents and, in particular, water.

The mass ratio of the isomers, 1-chloropropan-2-ol and 2-chloropropan-1-ol, is commonly greater than or equal to 0.01, preferably greater than or equal to 0.4. This ratio is commonly less than or equal to 99 and preferably less than or equal to 25.

In the process according to the invention, when the chlorohydrin is monochloroethanol, it is generally obtained in the form of a mixture of compounds comprising the 2-chloroethanol isomer. This mixture generally contains more than 1% by weight of the isomer, preferably more than 5% by weight and particularly more than 50%. The mixture commonly contains less than 99.9% by weight of the isomer, preferably less than 95% by weight and more particularly less than 90% by weight. The other constituents of the mixture may be compounds originating from the processes for preparing the chloroethanol, such as residual reactants, reaction by-products, solvents and, in particular, water.

In the process according to the invention, when the chlorohydrin is monochloropropanediol, it is generally obtained in the form of a mixture of compounds comprising the isomers of 1-chloropropane-2,3-diol and 2-chloropropane-1,3-diol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanediol, such as residual reactions, reaction by-products, solvents and, in particular, water.

The mass ratio between the 1-chloropropane-2,3-diol and 2-chloropropane-1,3-diol isomers is commonly greater than or equal to 0.01, preferably greater than or equal to 0.4. This ratio is commonly less than or equal to 99 and preferably less than or equal to 25.

In the process according to the invention, when the chlorohydrin is dichloropropanol, it is generally obtained in the form of a mixture of compounds comprising the isomers of 1,3-dichloropropan-2-ol and 2,3-dichloropropan-1-ol. This mixture generally contains more than 1% by weight of the two isomers, preferably more than 5% by weight and in particular more than 50%. The mixture commonly contains less than 99.9% by weight of the two isomers. The other constituents of the mixture may be compounds originating from the processes for preparing the dichloropropanol, such as residual reactants, reaction by-products, solvents and, in particular, water.

The mass ratio between the 1,3-dichloropropan-2-ol and 2,3-dichloropropan-1-ol isomers is commonly greater than or equal to 0.01, often greater than or equal to 0.4, frequently greater than or equal to 1.5, preferably greater than or equal to 3.0, more preferably greater than or equal to 7.0 and with very particular preference greater than or equal to 20.0. This ratio is commonly less than or equal to 99 and preferably less than or equal to 25.

The invention also provides a composition comprising 1,3-dichloropropan-2-ol and 2,3-dichloropropan-1-ol and other organic compounds and having a total 1,3-dichloropropan-2-ol and 2,3-dichloropropan-1-ol content, based on the total organic compounds content, of greater than or equal to 800 g/kg. Said content is often greater than or equal to 850 g/kg, frequently greater than or equal to 900 g/kg, in particular greater than or equal to 950 g/kg, specifically greater than or equal to 975 g/kg, and very particularly greater than or equal to 985 g/kg. This composition may also contain water and hydrogen chloride.

The chlorohydrin obtained in the process according to the invention may include a heightened amount of halogenated ketones, in particular of chloroacetone, as described in the patent application FR 05.05120 of May 20, 2005, filed in the name of the applicant, and the content of which is incorporated here by reference. The halogenated ketone content may be reduced by subjecting the chlorohydrin obtained in the process according to the invention to an azeotropic distillation in the presence of water or by subjecting the chlorohydrin to a dehydrochlorination treatment as described in this application from page 4 line 1 to page 6 line 35.

Particular mention is made of a process for preparing an epoxide wherein halogenated ketones are formed as by-products and which comprises at least one treatment of removal of at least a portion of the halogenated ketones formed. Mention is made more particularly of a process for preparing an epoxide by dehydrochlorinating a chlorohydrin of which at least one fraction is prepared by chlorinating a polyhydroxylated aliphatic hydrocarbon, an ester of a polyhydroxylated aliphatic hydrocarbon or a mixture thereof, a treatment of dehydrochlorination and a treatment by azeotropic distillation of a water/ketone mixture, which are intended to remove at least a portion of the halogenated ketones formed, and a process for preparing epichlorohydrin wherein the halogenated ketone formed is chloroacetone.

The chlorohydrin obtained in the process according to the invention may be subjected to a dehydrochlorination reaction in order to produce an epoxide, as described in the patent applications WO 2005/054167 and FR 05.05120, both filed in the name of SOLVAY SA.

The term "epoxide" is used herein to describe a compound containing at least one oxygen bridged on a carbon-carbon bond. Generally speaking, the carbon atoms of the carbon-carbon bond are adjacent and the compound may contain atoms other than carbon atoms and oxygen atoms, such as hydrogen atoms and halogens. The preferred epoxides are ethylene oxide, propylene oxide, glycidol, epichlorohydrin and mixtures of at least two thereof.

The dehydrochlorination of the chlorohydrin may be carried out as described in the application entitled "Process for preparing an epoxide starting from a polyhydroxylated aliphatic hydrocarbon and a chlorinating agent", filed in the name of SOLVAY SA on the same day as the present application, and the content of which is incorporated here by reference.

Particular mention is made of a process for preparing an epoxide wherein a reaction mixture resulting from the reaction between a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without intermediate treatment.

Mention is also made of the preparation of an epoxide that comprises the following steps:
(a) A polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture.
(b) At least a fraction of the reaction mixture obtained in step (a), this fraction having the same composition as the reaction mixture obtained in step (a), is subjected to one or more treatments in steps subsequent to step (a).
(c) A basic compound is added to at least one of the steps subsequent to step (a) in order to react at least partly with the chlorohydrin, the chlorohydrin esters, the chlorinating agent and the organic acid so as to form the epoxide and salts.

The process for producing the chlorohydrin according to the invention, may be integrated within an overall plan for preparation of an epoxide, as described in the application entitled "Process for preparing an epoxide starting from a chlorohydrin", filed in the name of SOLVAY SA on the same day as the present application, and the content of which is incorporated here by reference.

Particular mention is made of a process for preparing an epoxide that comprises at least one step of purification of the epoxide formed, the epoxide being at least partly prepared by a process of dehydrochlorinating a chlorohydrin, the latter being at least partly prepared by a process of chlorinating a polyhydroxylated aliphatic hydrocarbon, an ester of a polyhydroxylated aliphatic hydrocarbon or a mixture thereof.

In the process according to the invention, the polyhydroxylated aliphatic hydrocarbon is preferably glycerol and the chlorohydrin is preferably dichloropropanol.

When the chlorohydrin is dichloropropanol, the process according to the invention may be followed by preparation of epichlorohydrin by dehydrochlorination of dichloropropanol, and the epichlorohydrin may be used in the production of epoxy resins.

The example below is intended to illustrate the invention, though without subjecting it to any limitation.

SINGLE EXAMPLE

The example according to the invention was carried out in plant as per the diagram in FIG. 1. A reactor equipped with a stirring device (4) was supplied continuously with a stream of 20 kg/h of glycerol (1) and with a stream of 47.2 kg/h of 33% concentrated hydrochloric acid (2). The adipic acid serving as catalyst is introduced into the reactor via line (3). The reactor operated at a temperature of 125° C. and at atmospheric pressure with a reaction-liquid volume of 625.1. A distillation column (6) was supplied via line (5) with vapours produced in the reactor (4). A stream was withdrawn from column (6) via line (7) and was introduced into a condenser (8). The stream coming from condenser (8) was introduced via line (9) into a phase separator (10), in which it was separated into aqueous and organic phases. A fraction of the separated aqueous phase was recycled via line (11) to the top of column (6) in order to maintain a reflux sufficient for the separation. The less volatile compounds were condensed in the column and were recycled to reactor (4) via line (12). The production of dichloropropanol consisted of a dichloropropanol-saturated aqueous phase, which was withdrawn via line (13), and a water-saturated organic phase, which was withdrawn via line (14). The overall production of dichloropropanol, containing a small amount of hydrogen chloride, yielded an organic purity of 99.6% by weight.

A fraction of the reaction mixture was withdrawn at regular intervals via line (15) in order to maintain a constant liquid volume in reactor (4).

The overall steady-state catalyst content was 1.87 mol of weak acid and ester functions combined with the adipic acid per kg of reaction mixture.

The organic part of the constituents of the reaction mixture comprises 35.5 mol % of dichloropropanols and esters thereof, 48.5 mol % of monochloropropanediols and esters thereof, 5.5 mol % of glycerol and its esters, 9.1 mol % of diglycerols and of chlorinated diglycerols, and 1.4 mol % of acid.

The invention claimed is:

1. A continuous process for producing a chlorohydrin selected from the group consisting of chloropropanediol, dichloropropanol and a mixture thereof, wherein glycerol, an ester of glycerol or a mixture thereof is reacted with a chlorinating agent and an organic acid in a liquid reaction medium whose steady-state composition comprises glycerol and esters of glycerol whose sum content, expressed as moles of glycerol, is greater than 2.0 mol % and less than or equal to 30 mol %, the percentage being based on the organic part of the liquid reaction medium.

2. The process according to claim 1, wherein the composition of the liquid reaction medium in the steady state comprises the chlorohydrin and chlorohydrin esters whose sum content, expressed as moles of chlorohydrin, is greater than or equal to 10 mol % and less than or equal to 98 mol %, the percentage being based on the organic part of the liquid reaction medium.

3. The process according to claim 1, wherein the composition of the liquid reaction medium in the steady state further comprises chlorinated oligomers of glycerol and esters of chlorinated oligomers of glycerol whose sum content, expressed as moles of glycerol, is greater than or equal to 0.1 mol % and less than or equal to 20 mol %, the percentage being based on the organic part of the liquid reaction medium.

4. The process according to claim 1, wherein the chlorohydrin is a mixture of chloropropanediol and dichloropropanol.

5. The process according to claim 4, wherein the composition of the liquid reaction medium in the steady state comprises the chloropropanediol and chloropropanediol esters whose sum content, expressed as moles of chloropropanediol, is greater than or equal to 11 mol % and less than or equal to 85 mol %, the percentage being based on the organic part of the liquid reaction medium.

6. The process according to claim 4, wherein the composition of the liquid reaction medium in the steady state comprises the dichloropropanol and dichloropropanol esters whose sum content, expressed as moles of dichloropropanol, is greater than or equal to 0.5 mol % and less than or equal to 79 mol %, the percentage being based on the organic part of the liquid reaction medium.

7. The process according to claim 1, wherein the glycerol, the ester of glycerol or the mixture thereof is obtained starting from renewable raw materials.

8. The process according to claim 1, wherein the chlorinating agent is gaseous hydrogen chloride.

9. The process according to claim 1, wherein the organic acid is an impurity present in the glycerol, the ester of glycerol or the mixture thereof.

10. The process according to claim 1, wherein the organic acid is used as a catalyst of the chlorination reaction.

11. The process according to claim 3, wherein the esters of glycerol, of the chlorohydrin and of the chlorinated oligomers of glycerol result from reactions of the organic acid with glycerol, the chlorohydrin and the chlorinated oligomers of glycerol.

12. The process according to claim 1, wherein said process produces at least some dichloropropanol, and further comprising preparation of epichlorohydrin by dehydrochlorination of dichloropropanol.

13. The process according to claim 12, further comprising using the epichlorohydrin in the production of an epoxy resin.

14. The process according to claim 1, wherein the organic acid is a carboxylic acid having an atmospheric boiling point of greater than or equal to 200° C.

15. The process according to claim 14, wherein the organic acid is adipic acid.

16. The process according to claim 1, wherein said glycerol, an ester of glycerol or a mixture thereof is reacted with a chlorinating agent and an organic acid at a temperature of at least 20° C. and not more than 160° C. in a liquid reaction medium.

17. The process according to claim 14, wherein said glycerol, an ester of glycerol or a mixture thereof is reacted with a chlorinating agent and an organic acid at a temperature of at least 20° C. and not more than 160° C., a pressure of at least 0.3 bar and not more than 100 bar, and for a residence time of at least 1 h and not more than 50 h, in a liquid reaction medium.

18. The process according to claim 15, wherein said glycerol, an ester of glycerol or a mixture thereof is reacted with a chlorinating agent and an organic acid at a temperature of at least 20° C. and not more than 160° C., a pressure of at least 0.3 bar and not more than 100 bar, and for a residence time of at least 1 h and not more than 50 h, in a liquid reaction medium.

* * * * *